(12) United States Patent
Jang et al.

(10) Patent No.: US 12,070,242 B2
(45) Date of Patent: Aug. 27, 2024

(54) TUBE BODY CLEANING APPARATUS

(71) Applicant: IUCF-HYU (INDUSTRY-UNIVERSITY COOPERATION FOUNDATION HANYANG UNIVERSITY), Seoul (KR)

(72) Inventors: Gunhee Jang, Seoul (KR); Na Hyun Kim, Seoul (KR); Eunsoo Jung, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 337 days.

(21) Appl. No.: 17/419,553

(22) PCT Filed: Nov. 19, 2019

(86) PCT No.: PCT/KR2019/015872
§ 371 (c)(1),
(2) Date: Jun. 29, 2021

(87) PCT Pub. No.: WO2020/141721
PCT Pub. Date: Jul. 9, 2020

(65) Prior Publication Data
US 2022/0071654 A1    Mar. 10, 2022

(30) Foreign Application Priority Data

Dec. 31, 2018 (KR) ........................ 10-2018-0173448
Jan. 29, 2019 (KR) ........................ 10-2019-0010970

(51) Int. Cl.
*A61B 17/3207* (2006.01)
*B08B 9/045* (2006.01)
(Continued)

(52) U.S. Cl.
CPC ........ *A61B 17/32075* (2013.01); *B08B 9/045* (2013.01); *A61B 2017/00367* (2013.01);
(Continued)

(58) Field of Classification Search
CPC .... A61B 17/32075; A61B 2017/00367; A61B 2017/00477; A61B 2017/320052;
(Continued)

(56) References Cited

U.S. PATENT DOCUMENTS

2001/0018596 A1* 8/2001 Selmon ................. A61M 29/02
606/198
2002/0019644 A1* 2/2002 Hastings ........ A61B 17/320758
606/41
(Continued)

FOREIGN PATENT DOCUMENTS

JP    6-122367 A    5/1994
JP    10-103583 A   4/1998
(Continued)

OTHER PUBLICATIONS

International Search Report for PCT/KR2019/015872 dated Feb. 26, 2020 (PCT/ISA/210).

*Primary Examiner* — Jing Rui Ou
(74) *Attorney, Agent, or Firm* — Sughrue Mion, PLLC (57) ABSTRACT

The present invention provides a tube body cleaning apparatus. A tube body cleaning apparatus according to the present invention comprises: a body having a set length and formed from a flexible material; a work member positioned at one point of the length direction of the body and rotatable, about a shaft provided in the length direction of the body, with respect to the body; and an expansion member positioned at one point of the length direction of the body and enabling a volume, which protrudes outward from the body, to increase by expanding.

4 Claims, 10 Drawing Sheets

(51) Int. Cl.
*A61B 17/00* (2006.01)
*A61B 17/32* (2006.01)

(52) U.S. Cl.
CPC ............... *A61B 2017/00477* (2013.01); *A61B 2017/00876* (2013.01); *A61B 2017/320052* (2013.01); *B08B 2209/04* (2013.01)

(58) Field of Classification Search
CPC .... A61B 2017/00876; A61B 17/32053; A61B 17/320758; A61B 2017/320775; B08B 9/045; B08B 2209/04
See application file for complete search history.

(56) References Cited

U.S. PATENT DOCUMENTS

| | | | | |
|---|---|---|---|---|
| 2002/0029056 A1* | 3/2002 | Hall | ............... | A61B 17/320758 606/80 |
| 2002/0138088 A1* | 9/2002 | Nash | ................ | A61B 17/32037 606/159 |
| 2005/0113853 A1* | 5/2005 | Noriega | ............. | A61B 17/3421 606/159 |
| 2006/0015126 A1* | 1/2006 | Sher | ............... | A61B 17/320758 606/159 |

FOREIGN PATENT DOCUMENTS

| | | |
|---|---|---|
| JP | 2004-283584 A | 10/2004 |
| JP | 2008-155140 A | 7/2008 |
| JP | 2009-243257 A | 10/2009 |
| JP | 4850429 B2 | 1/2012 |
| JP | 4993863 B2 | 8/2012 |
| JP | 4993982 B2 | 8/2012 |
| KR | 2010-0125610 A | 12/2010 |
| KR | 10-2011-0007917 A | 1/2011 |
| KR | 10-1687919 B1 | 12/2016 |
| KR | 10-1782744 B1 | 9/2017 |

* cited by examiner

TUBE BODY CLEANING APPARATUS

TECHNICAL FIELD

The present invention relates to a tube body cleaning apparatus, and more particularly, to a tube body cleaning apparatus capable of performing a work while being effectively fixed to a tube body.

BACKGROUND ART

In general, tube body cleaning apparatuses are used to observe a narrow intratubular environment that may not be viewed with a naked eye by connecting a camera to an end of a system. The tube body cleaning apparatus may be used to inspect and diagnose narrow spaces that are difficult to be viewed with the naked eye without any dismantlement or cutting in all fields across industries such as aviation, power plants, automobiles, machinery, shipping, heavy industry, and construction. Alternatively, the tube body cleaning apparatus may be used as a catheter for diagnosing and treating a disease by observing an internal environment of a human body, such as an internal organ and a blood vessel of the human body.

DISCLOSURE

Technical Problem

The present invention provides a tube body cleaning apparatus capable of effectively cleaning a tube body.

In addition, the present invention provides a tube body cleaning apparatus capable of performing a work while being effectively fixed to a periphery of a cleaning target region.

In addition, the present invention provides a tube body cleaning apparatus that may be effectively moved to the cleaning target region.

Technical Solution

According to the present invention, a tube body cleaning apparatus includes: a body having a set length, and formed of a flexible material; a work member located at one point of the body in a length direction of the body, and rotatable with respect to the body about an axis defined in the length direction of the body; and an expansion member located at one point of the body in the length direction, and configured to expand to increase a volume protruding outward from the body.

In addition, the work member may be located on a front side of the body, and movable back and forth with respect to the body.

In addition, the tube body cleaning apparatus may further include a support member configured to connect the body to the work member, a cylinder part may be formed inside a front end of the body, and the support member may include: a piston part movable back and forth within the cylinder part; and a support part connected to the piston part, and located outside the body.

In addition, the tube body cleaning apparatus may further include a magnetic member fixed to the support part.

In addition, the tube body cleaning apparatus may further include a guide magnetic member located at a front end of the body.

In addition, the work member may be spaced rearward from a front end of the body by a set distance, and the tube body cleaning apparatus may further include a work magnetic member located between the work member and the body, and fixedly coupled to the work member so as to be rotatable together with the work member.

In addition, the expansion member may include: a front expansion member located between the work magnetic member and the front end of the body; and a front fluid guide part connected to the front expansion member to supply a fluid for expansion into a space formed inside the front expansion member.

In addition, the tube body cleaning apparatus may further include a guide magnetic member located at the front end of the body on a front side of the front expansion member.

In addition, the expansion member may further include: a rear expansion member located rearward of the work magnetic member; and a rear fluid guide part connected to the rear expansion member to supply a fluid for expansion into a space formed inside the rear expansion member.

In addition, the body may include: a first frame formed in a rod shape having a set length; a second frame formed in a rod shape having a set length; and a connection part formed in a rod shape having a set length, in which the connection part has a smaller area of a section perpendicular to the length direction than each of the first frame and the second frame, and having one end connected to the first frame and an opposite end connected to the second frame, and the work magnetic member may be formed in a ring structure, and fitted to the connection part.

Advantageous Effects

According to one embodiment of the present invention, a tube body cleaning apparatus capable of effectively cleaning a tube body can be provided.

In addition, according to one embodiment of the present invention, a tube body cleaning apparatus capable of performing a work while being effectively fixed to a periphery of a cleaning target region can be provided.

In addition, according to one embodiment of the present invention, a tube body cleaning apparatus that may be effectively moved to the cleaning target region can be provided.

BEST MODE

According to the present invention, a tube body cleaning apparatus includes: a body having a set length, and formed of a flexible material; a work member located at one point of the body in a length direction of the body, and rotatable with respect to the body about an axis defined in the length direction of the body; and an expansion member located at one point of the body in the length direction, and configured to expand to increase a volume protruding outward from the body.

MODE FOR INVENTION

Hereinafter, embodiments of the present invention will be described in more detail with reference to the accompanying drawings. The embodiments of the present invention may be modified into various other forms, and the scope of the present invention should not be construed as being limited to the following embodiments. The present embodiment is provided to more completely describe the present invention to those of ordinary skill in the art. Therefore, in the drawings, a shape of an element has been exaggerated to emphasize a clearer description.

Figure 1:
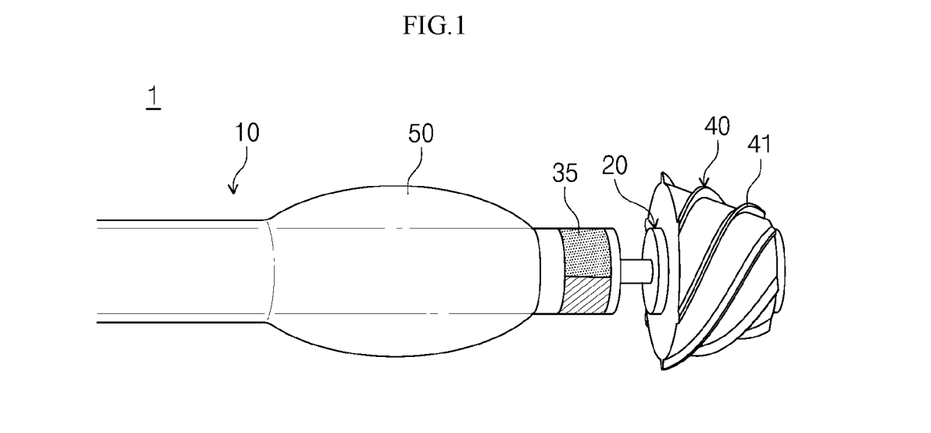
FIG. 1 is a view showing a tube body cleaning apparatus according to a first embodiment of the present invention.
Figure 2:
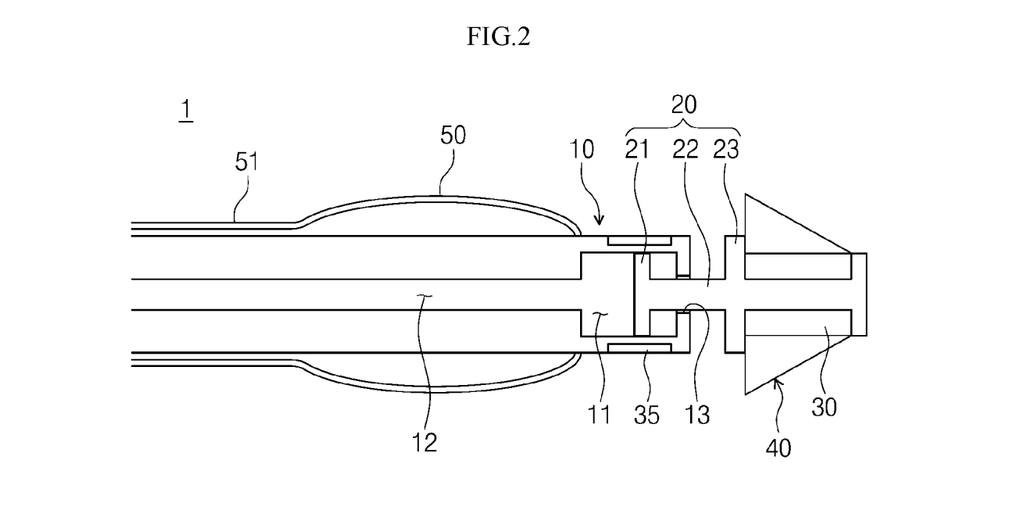
FIG. 2 is a sectional view showing the tube body cleaning apparatus of FIG. 1.

FIG. 1 is a view showing a tube body cleaning apparatus according to a first embodiment of the present invention, and FIG. 2 is a sectional view showing the tube body cleaning apparatus of FIG. 1.

Referring to FIGS. 1 and 2, a tube body cleaning apparatus 1 may include a body 10, a support member 20, a magnetic member 30, a work member 40, and an expansion member 50.

Hereinafter, a direction in which the tube body cleaning apparatus 1 moves when the tube body cleaning apparatus 1 approaches a cleaning target region (OP of FIG. 3) within a tube body (T of FIG. 3) to perform a work will be referred to as a forward direction.

The body 10 may be formed in a rod shape having a set length. A section of the body 10 perpendicular to a length direction of the body 10 may be formed in a circular shape, a polygonal shape, or the like. A cylinder part 11 may be formed inside a front end of the body 10. The cylinder part 11 may be configured as an empty space having a set volume. A section of the cylinder part 11 in a direction perpendicular to the length direction may be uniformly formed in the length direction. The cylinder part 11 may be connected to a driving fluid guide part 12. For example, the driving fluid guide part 12 may be configured as a flow path formed inside the body 10, and may have the same area of a section perpendicular to the length direction as the cylinder part 11 or a smaller area of the section perpendicular to the length direction than the cylinder part 11. In addition, the driving fluid guide part 12 may be formed in a piping structure and located on an outer surface of the body 10, and a front end of the fluid guide part 12 may be connected to the cylinder part 11. The body 10 may be formed of a flexible material.

The support member 20 may be connected to the front end of the body 10. The support member 20 may be movable back and forth with respect to the body 10. The support member 20 may include a piston part 21 and a support part 23.

The piston part 21 may be formed in a plate shape having an area corresponding to an area of the section of the cylinder part 11, and located in the cylinder part 11. The piston part 21 may be movable back and forth within the cylinder part 11 by a driving fluid supplied to the cylinder part 11 through the driving fluid guide part 12. The driving fluid supplied to control a position of the piston part 21 may be a liquid having stability against injection into a human body, such as physiological saline.

A connection part 22 having a rod shape may extend forward from a front surface of the piston part 21. The connection part 22 may be located in a connection hole 13, which is formed at the front end of the body 10 so as to be connected to the cylinder part 11, and a front end of the connection part 22 may be located outside the body 10.

The support part 23 may be connected to the front end of the connection part 22, and the magnetic member 30 may be fixed to the support part 23. For example, a support groove (not shown) may be formed in a ring shape in a circumferential direction of the support part 23, and the magnetic member 30 may be formed in a ring shape corresponding to the support groove so as to be located in the support groove. In this case, the magnetic member 30 may be fixed to the support part 23, or rotatable with respect to the support part 23. When the magnetic member 30 is fixed to the support part 23, the support member 20 may be rotatable with respect to the body 10. In addition, the support groove may be located in one area of the support part 23 in the circumferential direction, and the magnetic member 30 may be formed in a shape corresponding to the support groove so as to be located in the support groove. Further, at least two support grooves may be spaced apart from each other in the circumferential direction of the support part 23 by a set distance, and the magnetic member 30 may be located in each of the support grooves. The magnetic member 30 may be a permanent magnet. The magnetic member 30 may be configured such that an N-pole and an S-pole are arranged in the direction perpendicular to the length direction of the body 10. In addition, the magnetic member 30 may be configured such that the N-pole and the S-pole are arranged in the length direction of the body 10. Further, the magnetic member 30 may be configured such that the N-pole and the S-pole are arranged in a direction inclined with respect to the length direction of the body 10 by a set angle.

The work member 40 may be rotatable with respect to the body 10 about an axis defined in the length direction of the body 10 on a front side of the body 10. The work member 40 may be movable back and forth with respect to the body 10. The work member 40 may be connected to the support member 20 or the magnetic member 30 so as to be rotatable with respect to the body 10 together with the support member 20 or the magnetic member 30. For example, the work member 40 may be connected to an outer surface of the magnetic member 30. In detail, the work member 40 may be formed in a ring structure and located around an outer circumference of the magnetic member 30, or may be formed in an arc structure and located in a partial area around the outer circumference of the magnetic member 30. In addition, a plurality of work members 40 may be spaced apart from each other along the outer circumference of the magnetic member 30. As another example, the work member 40 may be located around an outer circumference of a front or rear end of the support part 23. In this case, the configuration of the work member 40 is not limited to a configuration that is physically separate from the magnetic member 30 or the support member 20. For example, the work member 40 may be configured as a component that is separate from the magnetic member 30 or the support member 20 and attached to the magnetic member 30 or the support member 20, and may be a component formed by processing a shape of a part of the magnetic member 30 or the support member 20.

The work member 40 may be configured such that a rear end of the work member 40 protrudes outward more as compared with a front end of the work member 40. For example, an outer surface of the work member 40 may be inclined toward an outside from a front side to a rear side of the work member 40.

A work part 41 may be formed on the outer surface of the work member 40. For example, the work part 41 may have roughness, such as grooves, concavo-convex portions, and protrusions having a spiral structure, so as to improve efficiency of a work of removing a substance attached to an inner surface of the tube body T or chipping away the inner surface of the tube body T as the work part 41 rotates in contact with the inner surface of the tube body T.

The expansion member 50 may be located at one point of the body 10 in the length direction. For example, the expansion member 50 may be located at the front end of the body 10 adjacent to the work member 40. The expansion member 50 may be formed in a ring shape around a circumference of the body 10, or may be configured in a form of at least one protrusion provided in a circumferential direction of the body 10. The expansion member 50 may expand to increase a volume protruding outward from the body 10.

The expansion member 50 may be connected to a fluid guide part 51. The fluid guide part 51 may supply a fluid for expansion into a space formed inside the expansion member 50. The fluid for expansion may be a liquid having stability against injection into a human body, such as physiological saline. FIG. 2 illustrates a case in which the fluid guide part 51 is located on the outer surface of the body 10 in the length direction of the body 10. However, a scheme of configuring the fluid guide part 51 is not limited the above-described scheme, and the fluid guide part 51 may be formed in a piping structure inside the body 10 in the length direction of the body 10.

A guide magnetic member 35 may be additionally provided at one point of the body 10 in the length direction. The guide magnetic member 35 may be directly fixed to the outer surface of the body 10, located in a groove formed in the outer surface of the body 10, or fixed to a structure located on the outer surface of the body 10.

The guide magnetic member 35 may be formed in a ring shape, or may be located in a partial area around an outer circumference of the body 10. In addition, at least two guide magnetic members 35 may be spaced apart from each other by a set distance in the circumferential direction of the body 10. The guide magnetic member 35 may be a permanent magnet. The guide magnetic member 35 may be configured such that an N-pole and an S-pole are arranged in the direction perpendicular to the length direction of the body 10. In addition, the guide magnetic member 35 may be configured such that the N-pole and the S-pole are arranged in the length direction of the body 10. Further, the guide magnetic member 35 may be configured such that the N-pole and the S-pole are arranged in a direction inclined with respect to the length direction of the body 10 by a set angle. The guide magnetic member 35 may be located at the front end of the body 10. For example, the guide magnetic member 35 may be located forward of the expansion member 50, or may be located in an area in which the expansion member 50 is formed.

FIGS. 3 to 7 are views showing a method of using the tube body cleaning apparatus of FIG. 1.

Figure 3:
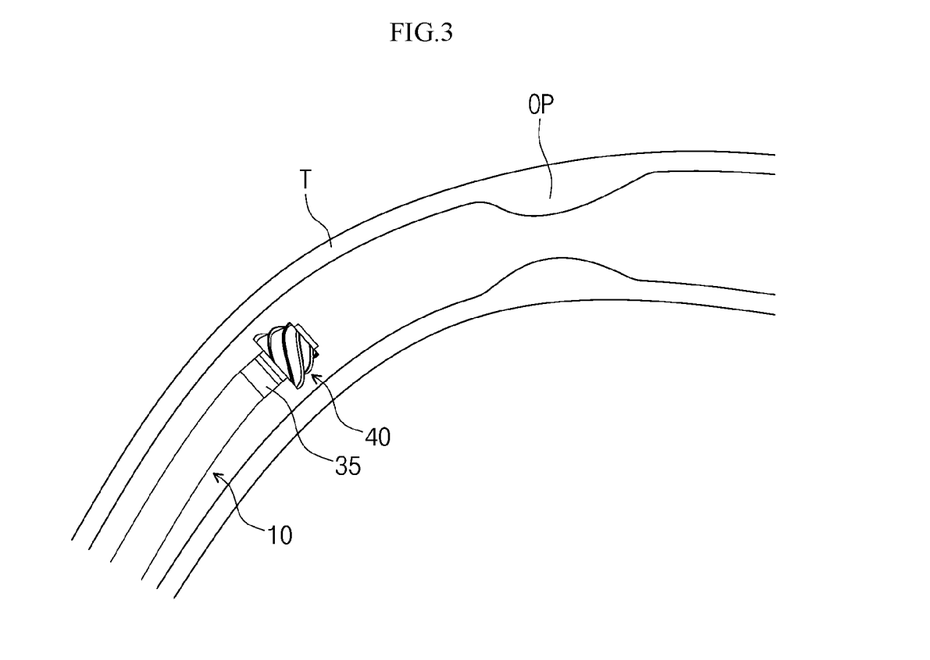
FIG. 3 is a view showing a state in which the tube body cleaning apparatus is moved to a cleaning target region in a tube body.

FIG. 3 is a view showing a state in which the tube body cleaning apparatus is moved to a cleaning target region in a tube body.

Referring to FIG. 3, first, after the tube body cleaning apparatus 1 is moved to a cleaning target region OP in the tube body T, a front region of the tube body cleaning apparatus 1 may be fixed to a periphery of the cleaning target region OP. The tube body T, which is a cleaning target, may be a blood vessel of a living body. A force for moving the tube body cleaning apparatus 1 forward within the tube body T may be provided by the guide magnetic member 35, the magnetic member 30, or the guide magnetic member 35 and the magnetic member 30.

In detail, when a magnetic field is applied to the guide magnetic member 35 or the magnetic member 30 from the outside of the tube body T, a force may act on the guide magnetic member 35 or the magnetic member 30 due to an interaction with the magnetic field. In addition, the magnetic field may be applied to the guide magnetic member 35 or the magnetic member 30 such that a torque may be generated, so that the tube body cleaning apparatus 1 may be rotated about the axis defined in the length direction to move within the tube body T while performing drilling motion. In this case, the torque generated in the guide magnetic member 35 or the magnetic member 30 may be represented by Formula 1 as follows.

$$T_e = m \times B_e \qquad \text{[Formula 1]}$$

(Magnetic field: $B_e$, $T_e$: Torque generated in magnetic member 30, m: Magnetic moment of magnetic member 30)

In addition, in order to generate the drilling motion, the magnetic field may be applied as follows.

$$B_e(t) = B_0(\cos(2\pi ft)U + \sin(2\pi ft)N \times U) \qquad \text{[Formula 2]}$$

($B_0$: Intensity of magnetic field, f: Rotation frequency, N: Unit vector of rotation axis, U: Unit vector perpendicular to rotation axis)

In this case, a position, a direction, a size, and the like of the magnetic field acting on the guide magnetic member 35 or the magnetic member 30 may be adjusted, so that the tube body cleaning apparatus 1 may move within the tube body T so as to move to the cleaning target region OP. In addition, the magnetic field may be applied to the guide magnetic member 35 and the magnetic member 30 while being individually controlled.

Figure 4:
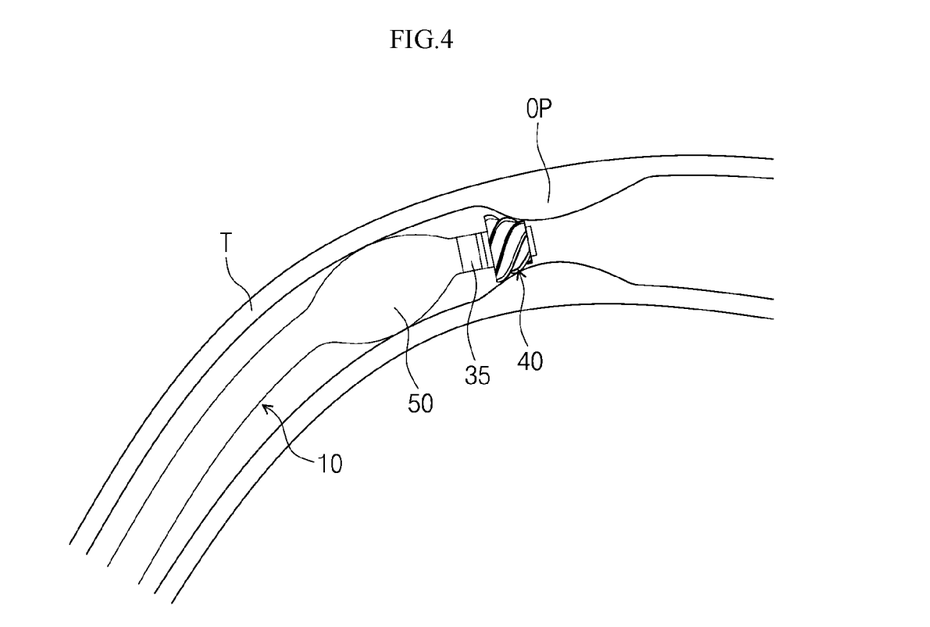
FIG. 4 is a view showing a state in which the tube body cleaning apparatus is fixed to a periphery of the cleaning target region.

FIG. 4 is a view showing a state in which the tube body cleaning apparatus is fixed to a periphery of the cleaning target region.

Referring to FIG. 4, when the work member 40 is moved so as to be located at the periphery of the cleaning target region OP, a fluid may be supplied through the fluid guide part 51 to expand the expansion member 50, so that the tube body cleaning apparatus 1 may be fixed. In this case, the expansion member 50 may preferably expand to the extent that the expansion member 50 and the inner surface of the tube body T are pressed against each other, so that the expansion member 50 may be prevented from being arbitrarily separated from a fixed position.

Figure 5:
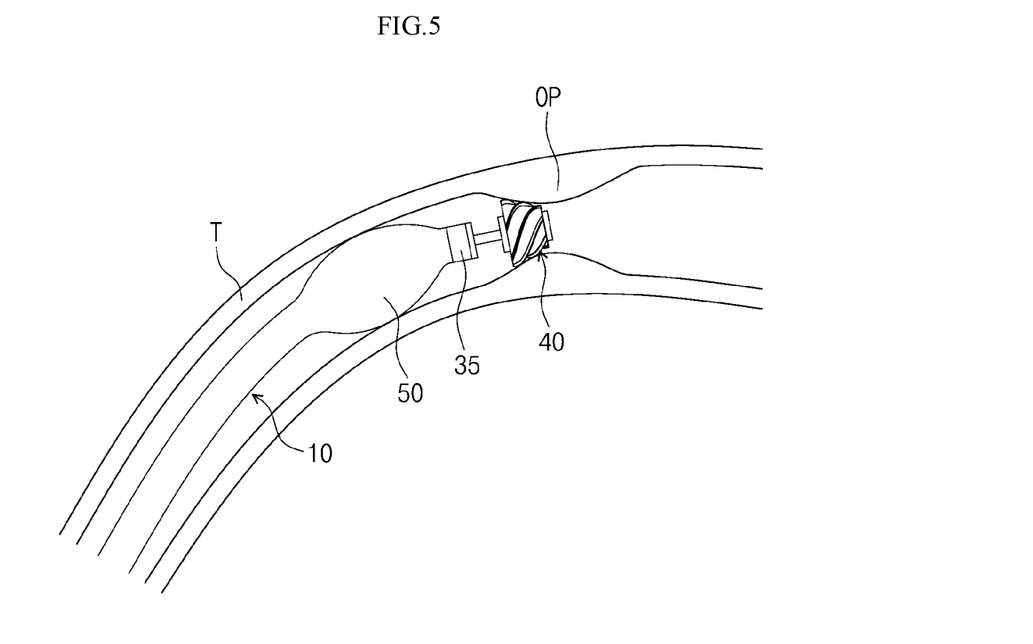
FIG. 5 is a view showing a state in which the tube body cleaning apparatus removes a substance attached to the tube body in the cleaning target region.

FIG. 5 is a view showing a state in which the tube body cleaning apparatus removes a substance attached to the tube body in the cleaning target region.

Referring to FIG. 5, when the tube body cleaning apparatus 1 is fixed, the driving fluid may be supplied to the cylinder part 11 through the driving fluid guide part 12 so as to move the support member 20 and the work member 40 forward. In addition, the magnetic field applied to the magnetic member 30 may be adjusted to generate a torque in the magnetic member 30, so that the magnetic member 30 and the work member 40 may be rotated.

When the work member 40 is rotated while the body 10 is not fixed to the tube body T, and when the body 10 is rotated while a position of the work member 40 in a forward-rearward direction with respect to the body 10 is fixed, there may be a limit to efficiency of removing the substance in the cleaning target region through the rotation of the work member 40. Meanwhile, according to the tube body cleaning apparatus 1 of an embodiment of the present invention, in a state in which the body 10 is fixed to the tube body T, the work member 40 may clean the tube body T by rotating while moving forward, so that the substance in the cleaning target region OP may be effectively removed.

Figure 6:
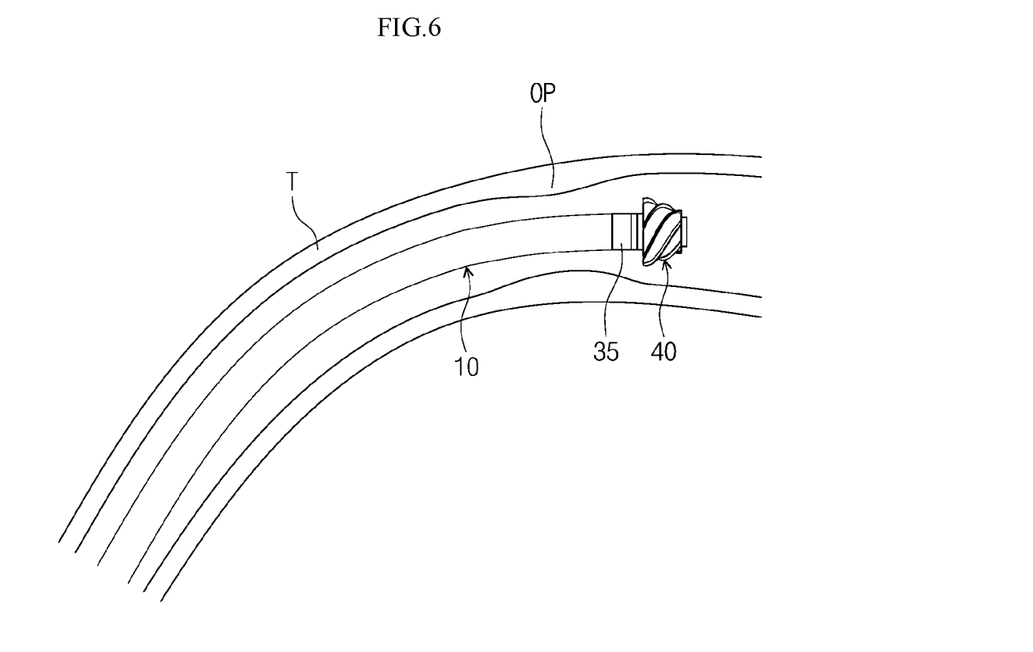
FIG. 6 is a view showing a state in which the tube body cleaning apparatus is additionally moved forward.
Figure 7:
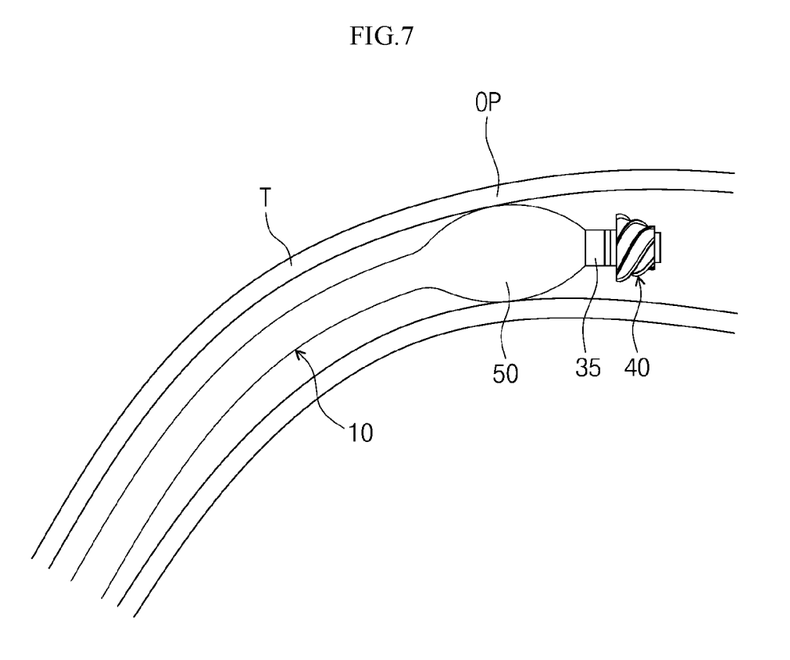
FIG. 7 is a view showing a state in which the cleaning target region is expanded through expansion of an expansion member.

FIG. 6 is a view showing a state in which the tube body cleaning apparatus is additionally moved forward, and FIG. 7 is a view showing a state in which the cleaning target region is expanded through expansion of an expansion member.

Referring to FIGS. 6 and 7, when the cleaning is performed by the drilling motion of the work member 40, the fluid of the expansion member 50 may be discharged through the fluid guide part 51, so that the expansion member 50 may be contracted. Thereafter, the tube body cleaning apparatus 1 may additionally move forward. In this case, a process of moving the tube body cleaning apparatus 1 forward may be the same as the process described above with reference to FIG. 3. When the expansion member 50 is located in the cleaning target region OP as the tube body cleaning apparatus 1 moves additionally, the fluid may be supplied to the expansion member 50 through the fluid guide part 51 so as to expand the expansion member 50. Accordingly, the cleaning target region OP of the tube body T may be expanded toward the outside, so that an area of the cleaning target region OP may be increased. Then, after the expansion member 50 is contracted, the tube body cleaning apparatus 1 may additionally move forward to perform a work, or may move rearward so as to be discharged out of the tube body T.

Figure 8:
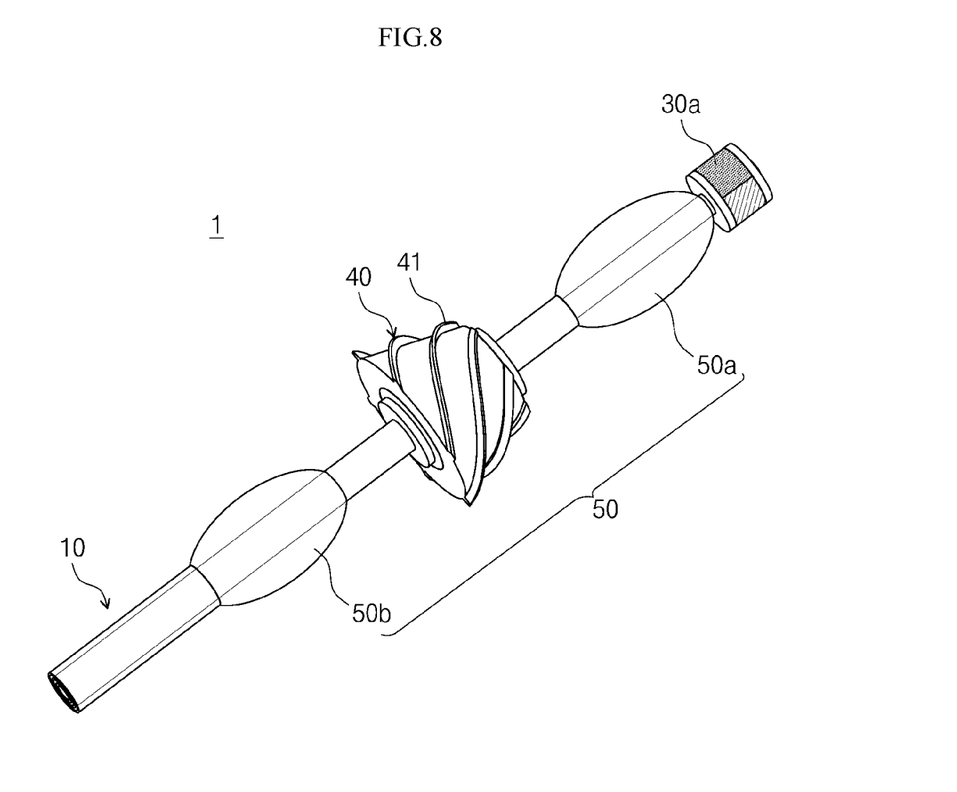
FIG. 8 is a view showing a tube body cleaning apparatus according to a second embodiment of the present invention.
Figure 9:
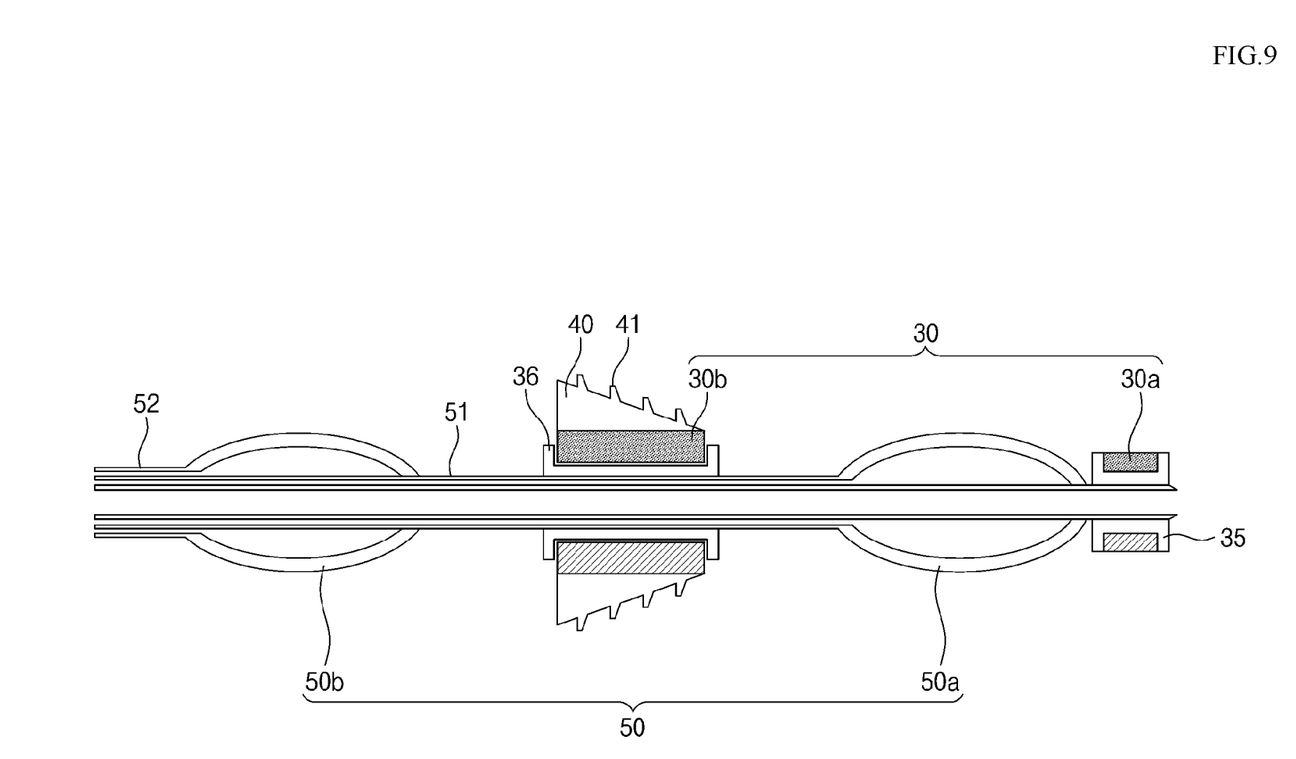
FIG. 9 is a sectional view showing the tube body cleaning apparatus of FIG. 8.

FIG. 8 is a view showing a tube body cleaning apparatus according to a second embodiment of the present invention, and FIG. 9 is a sectional view showing the tube body cleaning apparatus of FIG. 8.

Referring to FIGS. 8 and 9, a tube body cleaning apparatus 1 may include a body 10, a magnetic member 30, a work member 40, and an expansion member 50.

The body 10 may be formed in a rod shape having a set length. A front end of the body 10 may be tapered. A section of the body 10 perpendicular to a length direction of the body 10 may be formed in a circular shape, a polygonal shape, or the like. The body 10 may be formed in a hollow structure in which at least one area inside the structure is empty. For example, the body 10 may be formed in a tube structure having an inside that is empty in the length direction. The body 10 may be formed of a flexible material.

The magnetic member 30 may be located at one point in the length direction of the body 10. For example, support members 35 and 36 may be provided at one point in the length direction of the body 10. The support members 35 and 36 may be located outside the body 10, and the magnetic member 30 may be located in a support groove (not shown) formed on outer sides of the support members 35 and 36. The support groove may be formed in a ring shape in a circumferential direction of the body 10, and the magnetic member 30 may be formed in a ring shape corresponding to the support groove so as to be located in the support groove. In addition, the support groove may be located in one area of the body 10 in the circumferential direction on the support members 35 and 36, and the magnetic member 30 may be formed in a shape corresponding to the support groove so as to be located in the support groove. Further, at least two support grooves may be spaced apart from each other in the circumferential direction of the body 10 by a set distance, and the magnetic member 30 may be located in each of the support grooves. The magnetic member 30 may be a permanent magnet. The magnetic member 30 may be configured such that an N-pole and an S-pole are arranged in a direction perpendicular to the length direction of the body 10. In addition, the magnetic member 30 may be configured such that the N-pole and the S-pole are arranged in the length direction of the body 10. Further, the magnetic member 30 may be configured such that the N-pole and the S-pole are arranged in a direction inclined with respect to the length direction of the body 10 by a set angle.

The magnetic member 30 may include a guide magnetic member 30a and a work magnetic member 30b.

The guide magnetic member 30a may be located at the front end of the body 10. The guide magnetic member 30a may be located on a guide support member 35 located at the front end of the body 10 with the above-described structure. The guide magnetic member 30a may be fixed to the body 10. In addition, the guide magnetic member 30a may be fixed to the guide support member 35.

The work magnetic member 30b may be spaced rearward from the front end of the body 10 by a set distance so as to be located at one point in the length direction of the body 10. The work magnetic member 30b may be rotatable with respect to the body 10 about an axis defined in the length direction of the body 10. For example, the work magnetic member 30b may be located on a work support member 36 with the above-described structure, and the work support member 36 may be rotatable with respect to the body 10. In addition, a support groove may be formed in a ring shape in the work support member 36, and the work magnetic member 30b may be formed in a ring shape corresponding to the support groove so as to be rotatably located in the support groove.

The work member 40 may be rotatable with respect to the body 10 about the axis defined in the length direction of the body 10 at one point in the length direction of the body 10. The work member 40 may be connected to the work magnetic member 30b so as to be rotatable with respect to the body 10 together with the work magnetic member 30b. For example, the work member 40 may be connected to an outer surface of the work magnetic member 30b. In detail, the work member 40 may be formed in a ring structure and located around an outer circumference of the work magnetic member 30b, or may be formed in an arc structure and located in a partial area around the outer circumference of the work magnetic member 30*b*. In addition, a plurality of work members 40 may be spaced apart from each other along the outer circumference of the work magnetic member 30*b*. In this case, the configuration of the work member 40 is not limited to a configuration that is physically separate from the work magnetic member 30*b*. For example, the work member 40 may be configured as a component that is separate from the work magnetic member 30*b* and attached to the work magnetic member 30*b*, and may be a component formed by processing a shape of a part of the work magnetic member 30*b*.

The work member 40 may be configured such that a rear end of the work member 40 protrudes outward more as compared with a front end of the work member 40. For example, an outer surface of the work member 40 may be inclined toward an outside from a front side to a rear side of the work member 40.

A work part 41 may be formed on the outer surface of the work member 40. For example, the work part 41 may have roughness, such as grooves, concavo-convex portions, and protrusions having a spiral structure, so as to improve efficiency of a work of removing a substance attached to an inner surface of a tube body T or chipping away the inner surface of the tube body T as the work part 41 rotates in contact with the inner surface of the tube body T.

The expansion member 50 may be located at one point of the body 10 in the length direction. The expansion member 50 may be formed in a ring shape around a circumference of the body 10, or may be configured in a form of at least one protrusion provided in a circumferential direction of the body 10. The expansion member 50 may expand to increase a volume protruding outward from the body 10.

The expansion member 50 may include a front expansion member 50*a* and a rear expansion member 50*b*.

The front expansion member 50*a* may be located in a front region of the body 10. The front expansion member 50*a* may be located forward of the work magnetic member 30*b* and the work member 40. The front expansion member 50*a* may be located rearward of the guide magnetic member 30*a*. The front expansion member 50*a* may be connected to a front fluid guide part 51. The front fluid guide part 51 may supply a fluid for expansion to a space formed inside the front expansion member 50*a*. The fluid for expansion may be a liquid having stability against injection into a human body, such as physiological saline. FIG. 9 illustrates a case in which the front fluid guide part 51 is located on an outer surface of the body 10 in the length direction of the body 10. However, a scheme of configuring the front fluid guide part 51 is not limited to the above-described scheme, and the front fluid guide part 51 may be located in a space formed inside the body 10 in the length direction of the body 10, may be located on an inner surface of the body 10, or may be formed in a piping structure inside the body 10.

The rear expansion member 50*b* may be spaced rearward from the front expansion member 50*a* by a set distance. The rear expansion member 50*b* may be located rearward of the work magnetic member 30*b* and the work member 40. The rear expansion member 50*b* may be connected to a rear fluid guide part 52. The rear fluid guide part 52 may supply a fluid for expansion to a space formed inside the rear expansion member 50*b*. The fluid for expansion may be a liquid having stability against injection into a human body, such as physiological saline. FIG. 9 illustrates a case where the rear fluid guide part 52 is located on an outer surface of the front fluid guide part 51 in the length direction of the body 10. However, a scheme of configuring the rear fluid guide part 52 is not limited to the above-described scheme, and the rear fluid guide part 52 may be located on the outer surface of the body 10 in a region other than the front fluid guide part 51 in the length direction of the body 10, may be located in a space formed inside the body 10, may be located on an inner surface of the body 10, or may be formed in a piping structure inside the body 10.

FIGS. 10 to 13 are views showing a method of using the tube body cleaning apparatus of FIG. 8.

Figure 10:
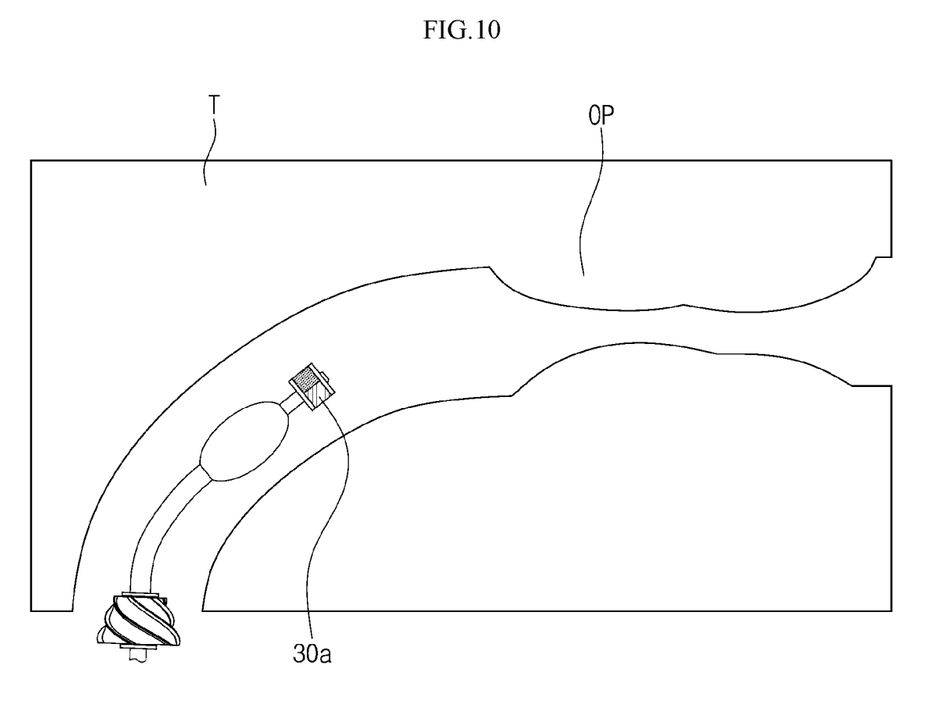
FIG. 10 is a view showing a state in which the tube body cleaning apparatus is moved to a cleaning target region in a tube body.
Figure 11:
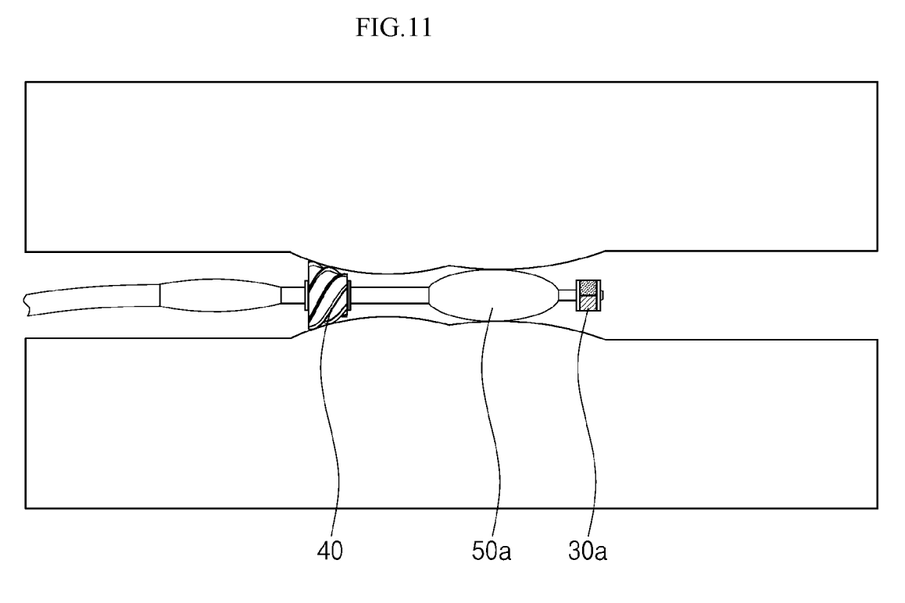
FIG. 11 is a view showing a state in which a front region of the tube body cleaning apparatus is fixed to a periphery of the cleaning target region.

FIG. 10 is a view showing a state in which the tube body cleaning apparatus is moved to a cleaning target region in a tube body, and FIG. 11 is a view showing a state in which a front region of the tube body cleaning apparatus is fixed to a periphery of the cleaning target region.

Referring to FIGS. 10 and 11, first, after the tube body cleaning apparatus 1 is moved to a cleaning target region OP in the tube body T, a front region of the tube body cleaning apparatus 1 may be fixed to a periphery of the cleaning target region OP. The tube body T, which is a cleaning target, may be a blood vessel of a living body. A force for moving the tube body cleaning apparatus 1 forward within the tube body T may be provided by the magnetic member 30. In detail, when a magnetic field is applied to the magnetic member 30 from the outside of the tube body T, a force may act on the magnetic member 30 due to an interaction with the magnetic field. In addition, the magnetic field may be applied to the magnetic member 30 such that a torque may be generated, so that the tube body cleaning apparatus 1 may be rotated about the axis defined in the length direction to move within the tube body T while performing a drilling motion. In this case, the torque generated in the magnetic member 30 may be represented by Formula 1 described above.

In addition, in order to generate the drilling motion, the magnetic field may be applied according to Formula 2 as described above.

In this case, a position, a direction, a size, and the like of the magnetic field acting on the magnetic member 30 may be adjusted, so that the tube body cleaning apparatus 1 may move within the tube body T so as to move to the cleaning target region OP. In addition, the magnetic field may be applied to the guide magnetic member 30*a* and the work magnetic member 30*b* while being individually controlled. Accordingly, due to a force applied to the guide magnetic member 30*a* and a force applied to the work magnetic member 30*b*, the tube body cleaning apparatus 1 may be controlled to move to a work target region such that the body 10 is bent to correspond to a shape of the tube body T during a movement process.

When the work member 40 is moved so as to be located at the periphery of the cleaning target region OP, a fluid may be supplied through the front fluid guide part 51 to expand the front expansion member 50*a*, so that the front region of the tube body cleaning apparatus 1 may be fixed. In this case, the front expansion member 50*a* may preferably expand to the extent that the front expansion member 50*a* and the inner surface of the tube body T are pressed against each other, so that the front expansion member 50*a* may be prevented from being arbitrarily separated from a fixed position.

Figure 12:
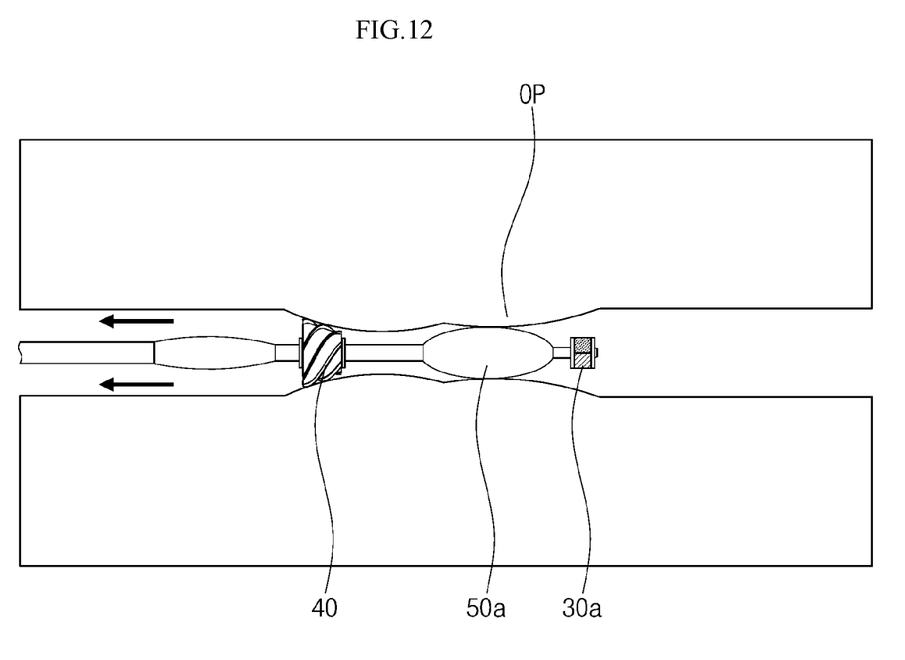
FIG. 12 is a view showing a state in which a position of the tube body cleaning apparatus is adjusted with respect to the tube body.
Figure 13:
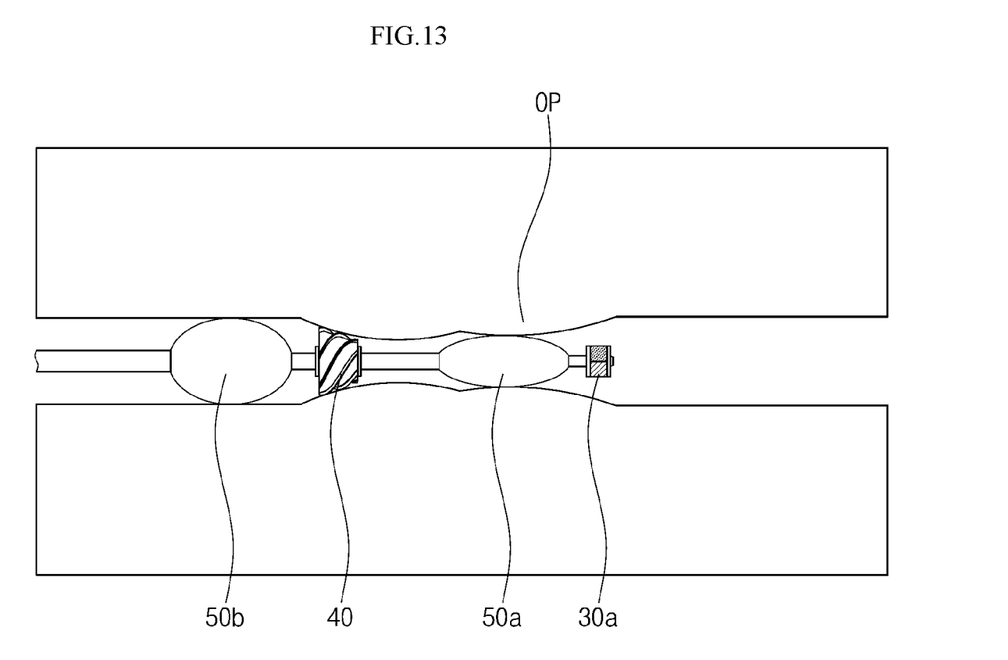
FIG. 13 is a view showing a state in which a rear expansion member expands.

FIG. 12 is a view showing a state in which a position of the tube body cleaning apparatus is adjusted with respect to the tube body, and FIG. 13 is a view showing a state in which a rear expansion member expands.

Referring to FIGS. 12 and 13, when the front region of the tube body cleaning apparatus 1 is fixed, the tube body cleaning apparatus 1 may be located with respect to the tube body T. When the front region of the tube body cleaning apparatus 1 is fixed, a direction of a rotation axis of the work member 40 may be misaligned with a length direction of the tube body T in a region where the work member 40 is located. When a force is applied to the tube body cleaning apparatus 1 in a rearward direction, the body 10 of the tube body cleaning apparatus 1 may be stretched tight. In this case, a degree of misalignment between the rotation axis of the work member 40 and the length direction of the tube body T may be corrected. In this state, the rear expansion member 50b may expand to additionally fix the tube body cleaning apparatus 1. Thereafter, a torque may be generated in the work magnetic member 30b through the magnetic field applied to the work magnetic member 30b, so that the work magnetic member 30b and the work member 40 may be rotated. Accordingly, the inner surface of the tube body T may be cleaned by the work member 40.

According to one embodiment of the present invention, after the tube body cleaning apparatus 1 is moved to the cleaning target region OP within the tube body T, a position of cleaning apparatus 1 may be fixed by the tube body expansion member 50. Accordingly, at an unintended time point, such as when the tube body T is cleaned as the work member 40 rotates, the tube body cleaning apparatus 1 may be prevented from being moved by a force due to the fluid flowing through the tube body T, a force acting on the work member 40 in a work process, and the like.

In addition, according to one embodiment of the present invention, the rotation axis of the work member 40 may be fixed by the front expansion member 50a and the rear expansion member 50b. Accordingly, when the tube body T is cleaned, a direction in which the rotation axis of the work member 40 is directed may be prevented from being arbitrarily changed by the force applied to the work member 40.

Figure 14:
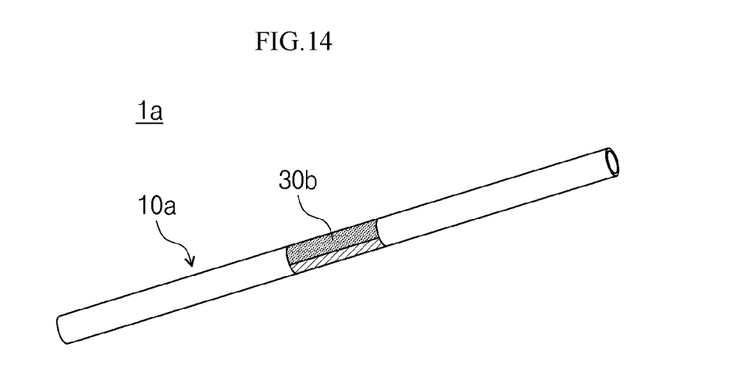
FIG. 14 is a perspective view showing a portion in which a magnetic member is located in a tube body cleaning apparatus according to another embodiment.
Figure 15:
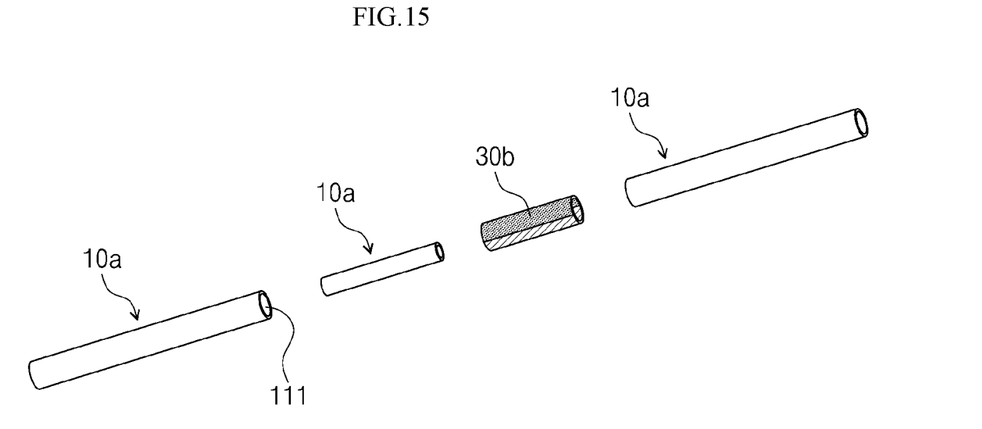
FIG. 15 is an exploded perspective view showing a portion in which the magnetic member is located in the tube body cleaning apparatus of FIG. 14.

FIG. 14 is a perspective view showing a portion in which a magnetic member is located in a tube body cleaning apparatus according to another embodiment, and FIG. 15 is an exploded perspective view showing a portion in which the magnetic member is located in the tube body cleaning apparatus of FIG. 14.

Since a configuration and a function of a tube body cleaning apparatus 1a according to FIGS. 14 and 15 are identical or similar to the configuration and the function of the tube body cleaning apparatus 1 of FIG. 8 except for a portion where the magnetic member 30b is located, redundant descriptions thereof will omitted, so that components corresponding thereto have been omitted in FIGS. 14 and 15.

Referring to FIGS. 14 and 15, a body 10a may include a first frame 110 and a second frame 120.

The first frame 110 may be formed in a rod shape having a set length. A section of the first frame 110 perpendicular to a length direction of the first frame 110 may be formed in a circular shape, a polygonal shape, or the like. The first frame 110 may be formed of a flexible material. A first insertion part 111 having a depth that is greater than or equal to a set value in the length direction may be formed at one end of the first frame 110. For example, the first insertion part 111 may be configured as a groove having a set depth in the length direction. In addition, the first frame 110 may be formed in a tube structure, so that an inner space of the first frame 110 formed in the length direction may be configured as the first insertion part 111.

The second frame 120 may be foamed in a rod shape having a set length. A section of the second frame 120 perpendicular to the length direction may correspond to the first frame 110. The second frame 120 may be formed of a flexible material. A second insertion part (not shown) having a depth that is greater than or equal to a set value in the length direction may be formed at one end of the second frame 120. For example, the second insertion part may be configured as a groove having a set depth in the length direction. In addition, the second frame 120 may be formed in a tube structure, so that an inner space of the second frame 120 formed in the length direction may be configured as the second insertion part.

The first frame 110 and the second frame 120 may be connected to each other by a connection part 130. The connection part 130 may be formed in a rod shape having a set length. The connection part 130 may be formed of a flexible material. The connection part 130 may have a smaller area of a section perpendicular to the length direction than each of the first frame 110 and the second frame 120. The magnetic member 30b formed in a ring structure may be fitted to the connection part 130, one end of the connection part 130 may be fitted to the first insertion part 111 so as to be connected to the first frame 110, and an opposite end of the connection part 130 may be fitted to the second insertion part so as to be connected to the second frame 120. The magnetic member 30b may have an outer circumference having a shape corresponding to an outer circumference of each of the first frame 110 and the second frame 120. The magnetic member 30b may be fixed to the connection part 130 so as to be configured as the guide magnetic member 30a described above, or may be rotatable with respect to the connection part 130 so as to be configured as the work magnetic member 30b described above.

According to the tube body cleaning apparatus 1a of one embodiment of the present invention, the outer circumference of the magnetic member 30b may correspond to an outer circumference of the body 10a. Accordingly, a size of the outer circumference of the tube body cleaning apparatus 1a may be reduced.

In addition, according to the tube body cleaning apparatus 1a of one embodiment of the present invention, the magnetic member 30b may be directly connected to the body 10a that is formed of a flexible material. Accordingly, flexibility of the tube body cleaning apparatus 1a may be increased, and the tube body cleaning apparatus 1a may be prevented from being damaged while the tube body cleaning apparatus 1a is bent.

According to another embodiment, the connection part 130 may be connected to one end of the first frame 110. Accordingly, the first frame 110 may be connected to the second frame 120 such that the connection part 130 is inserted into the insertion part of the second frame 120 while being fitted to the magnetic member 30b.

The above detailed description of the present invention has been provided for illustrative purposes. In addition, preferred embodiments of the present invention are shown and described in the above description, and the present invention may be used in various other combinations, modifications, and environments. In other words, changes or modifications can be made within the scope of the concept of the invention disclosed in the present disclosure, the scope equivalent to the above-disclosed contents, and/or the scope of the skill or knowledge in the art. The above embodiments describe the best mode for implementing the technical idea of the present invention, and various changes required in the specific application fields and uses of the present invention can be made to the embodiments.

Therefore, the detailed description of the invention is not intended to restrict the present invention to the disclosed embodiments. In addition, the appended claims should be construed as encompassing other embodiments.

INDUSTRIAL APPLICABILITY

The tube body cleaning apparatus according to the present invention may be used for a treatment in a blood vessel of a living body.

The invention claimed is:

1. A tube body cleaning apparatus comprising:
   a body having a set length, and formed of a flexible material;
   a work member located at one point of the body in a length direction of the body, and rotatable with respect to the body about an axis defined in the length direction of the body; and
   a support member configured to connect the body to the work member,
   wherein a cylinder part is formed inside a front end of the body as an empty space,
   wherein a driving fluid guide part is formed inside the body and connected to the cylinder part, and
   wherein the support member comprises:
      a piston part disposed within the cylinder part;
      a support part located outside the body;
      a connection part connecting the piston part to the support part; and
      a magnetic member fixed to the support part and coupled to the work member,
      wherein the piston part is movable back and forth within the cylinder part by a driving fluid supplied to the cylinder part through the driving fluid guide part.

2. The tube body cleaning apparatus of claim 1, wherein the working member is provided along an outer circumference of the magnetic member in a ring shape, fixedly coupled to the magnetic member, and gradually increased in diameter from a front end of the working member to a rear end of the working member, having protrusions formed on an outer surface of the working member.

3. The tube body cleaning apparatus of claim 2, when a magnetic field is applied from the outside, the magnetic member and the working member rotate together around the axis of the support part to perform a drilling motion.

4. The tube body cleaning apparatus of claim 1, further comprising a guide magnetic member located at the front end of the body.

* * * * *